United States Patent
Coughlan et al.

(12) 
(10) Patent No.: US 6,177,613 B1
(45) Date of Patent: Jan. 23, 2001

(54) SEED-PREFERRED PROMOTER

(75) Inventors: Sean J. Coughlan, Hockessin, DE (US); Ronnie J. Winfrey, Jr., Des Moines, IA (US)

(73) Assignee: Pioneer Hi-Bred International, Inc., Des Moines, IA (US)

(*) Notice: Under 35 U.S.C. 154(b), the term of this patent shall be extended for 0 days.

(21) Appl. No.: 09/227,794

(22) Filed: Jan. 8, 1999

(51) Int. Cl.[7] .............................. C12N 5/04; C12N 15/82; C12N 15/90; A01H 5/00; A01H 5/10

(52) U.S. Cl. .................. 800/287; 435/69.1; 435/320.1; 435/414; 435/415; 435/416; 536/24.1; 800/312; 800/314; 800/317; 800/317.3; 800/322

(58) Field of Search ............................. 435/69.1, 320.1, 435/410, 412, 414, 415, 416, 419, 468; 536/23.6, 24.1; 800/278, 281, 287, 295, 298, 312, 314, 317.3, 320, 320.1, 320.2, 320.3, 322

(56) References Cited

PUBLICATIONS

Kim et al, Plant Mol. Biol., vol. 24, pp. 105–117, 1994.*
Grossi et al, Plant Sci., vol. 103, pp. 189–198, 1994.*
Kodama et al, Plant Physiol., vol. 107, pp. 1177–1185, 1995.*
Marcellino et al, FEBS Lett., vol. 385, pp. 154–158, 1996.*
Fromm et al, Bio/Technol., vol. 8, pp. 833–839, 1990.*
Fromm et al., "Inheritance and Expression of Chimeric Genes in the Progeny of Transgenic Maize Plants", *Bio/Technology,* 8:833–839 (1990).
Grossi de Sa et al., "Functional studies on a seed–specific promoter from Brazil nut 2S gene", *Plant Science,* 103:189–198 (1994).
Kim et al., "A 20 nucleotide upstream element is essential for the nopaline synthase (nos) promoter activity", *Plant Molecular Biology,* 24:105–117 (1994).
Kodama et al., "Fatty Acid Desaturation during Chilling Acclimation is One of the Factors Involved in Conferring Low–Temperature Tolerance to Young Tobacco Leaves", *Plant Physiol.,* 107:117–1185 (1995).
Marcellino et al., "Modified 2S albumins with improved tryptophan content are correctly expressed in transgenic tobacco plants", FEBS Letters, 385:154–158 (1996).

* cited by examiner

*Primary Examiner*—Paula K. Hutzell
*Assistant Examiner*—Ashwin D. Mehta
(74) *Attorney, Agent, or Firm*—Pioneer Hi-Bred International, Inc.

(57) ABSTRACT

The present invention provides a composition and method for regulating expression of heterologous nucleotide sequences in a plant. The composition is a novel nucleic acid sequence for a seed-preferred promoter. A method for expressing a heterologous nucleotide sequence in a plant using the promoter sequence is also provided. The method comprises transforming a plant cell to contain a heterologous nucleotide sequence operably linked to the seed-preferred promoter of the present invention and regenerating a stably transformed plant from the transformed plant cell.

15 Claims, No Drawings

SEED-PREFERRED PROMOTER

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably linked promoter that is functional within the plant host. Choice of the promoter sequence will determine when and where within the organism the heterologous DNA sequence is expressed. Where continuous expression is desired throughout the cells of a plant, constitutive promoters are utilized. In contrast, where gene expression in response to a stimulus is desired, inducible promoters are the regulatory element of choice. Where expression in specific tissues or organs are desired, tissue-specific promoters are used. That is, these promoters can drive expression in specific tissues or organs. Additional regulatory sequences upstream and/or downstream from the core promoter sequence can be included in expression cassettes of transformation vectors to bring about varying levels of expression of heterologous nucleotide sequences in a transgenic plant.

Isolation and characterization of seed-preferred promoters that can serve as regulatory elements for expression of heterologous nucleotide sequences of interest in a seed-preferred manner are needed for improving seed traits in plants.

SUMMARY OF THE INVENTION

It is an object of the present invention to provide a novel nucleotide sequence for modulating gene expression in a plant.

It is a further object of the present invention to provide an isolated promoter capable of driving transcription in a seed-preferred manner.

It is a further object of the present invention to provide a method of improved control of an endogenous or exogenous product in the seed of a transformed plant.

It is a further object of the present invention to provide a method for providing useful changes in the phenotype of a seed of a transformed plant.

It is a further object of the present invention to provide a method for producing a novel product in the seed of a transformed plant.

It is a further object of the present invention to provide a method for producing a novel function in the seed of a transformed plant.

Therefore, in one aspect, the present invention relates to an isolated nucleic acid comprising a member selected from the group consisting of:

a) nucleic acids driving expression of the polynucleotide encoding soybean albumin;

b) nucleic acids comprising a functional variant or fragment of at least 20 contiguous nucleotides of the sequence set forth in SEQ ID NO 1;

c) the nucleic acids set forth in SEQ ID NO 1;

d) nucleic acids that hybridize to any one of a), b), or c), under stringent conditions; wherein stringent conditions include: a hybridization at 42° C. in a solution of 50%(w/v) formamide, 6x SSC, 0.5% SDS, 100 ug/ml salmon sperm, washed with 0.5% SDS and 2xSSC at 65° C. for 30 minutes and repeated;

e) nucleic acids having at least 65% sequence identity to SEQ ID NO 1 wherein the % sequence identity is based on the entire sequence and is determined by BLAST analysis under default parameters.

In other aspects, the present invention relates to expression cassettes comprising the promoter operably linked to a nucleotide sequence, vectors containing the expression cassette, and plants stably transformed with at least one expression cassette.

In a further aspect, the present invention relates to a method for modulating expression in the seed of a stably transformed plant comprising the steps of (a) transforming a plant cell with an expression cassette comprising the promoter of the present invention operably linked to at least one nucleotide sequence; (b) growing the plant cell under plant growing conditions and (c) regenerating a stably transformed plant from the plant cell wherein expression of the nucleotide sequence alters the phenotype of the seed.

DETAILED DESCRIPTION OF THE INVENTION

In accordance with the invention, a nucleotide sequence is provided that allows initiation of transcription in seed. The sequence of the invention comprises transcriptional initiation regions associated with seed formation and seed tissues. Thus, the compositions of the present invention comprise a novel nucleotide sequence for a plant promoter, more particularly a seed-preferred promoter for the gene AL3 (soybean 2S albumin pre-propeptide).

By "seed-preferred" is intended favored expression in the seed, including at least one of embryo, kernel, pericarp, endosperm, nucellus, aleurone, pedicel, and the like.

By "heterologous nucleotide sequence" is intended a sequence that is not naturally occurring with the promoter sequence. While this nucleotide sequence is heterologous to the promoter sequence, it may be homologous (native) or heterologous (foreign) to the plant host.

By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' untranslated region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired tissue such as the seed can be identified, isolated, and used with other core promoters to confirm seed-preferred expression.

The isolated promoter sequence of the present invention can be modified to provide for a range of expression levels of the heterologous nucleotide sequence. Less than the entire promoter region can be utilized and the ability to drive seed-preferred expression retained. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence.

It is recognized that to increase transcription levels enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoter of the present invention can be isolated from the 5' untranslated region flanking its respective transcription initiation site. The term "isolated" refers to material, such as a nucleic acid or protein, which is: (1) substantially or essentially free from components which normally accompany or interact with the material as found in its naturally occurring environment or (2) if the material is in its natural environment, the material has been altered by deliberate human intervention to a composition and/or placed at a locus in a cell other than the locus native to the material. Methods for isolation of promoter regions are well known in the art. One method is described in U.S. patent application Ser. No. 09/387,720 (pending) filed Aug. 31, 1998 herein incorporated by reference. The sequence for the promoter region is set forth in SEQ ID NO1.

The promoter region of the invention may be isolated from any plant, including, but not limited to corn (*Zea mays*), canola (*Brassica napus,* Brassica rapa ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (Cofea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), oats, barley, vegetables, ornamentals, and conifers. Preferably, plants include corn, soybean, sunflower, safflower, canola, wheat, barley, rye, alfalfa, and sorghum.

Promoter sequences from other plants may be isolated according to well known techniques based on their sequence homology to the promoter sequence set forth herein. In these techniques, all or part of the known promoter sequence is used as a probe which selectively hybridizes to other sequences present in a population of cloned genomic DNA fragments (i.e. genomic libraries) from a chosen organism. Methods are readily available in the art for the hybridization of nucleic acid sequences.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g. Innis et al. (1990)*PCR Protocols, A Guide to Methods and Applications,* eds., Academic Press).

The terms "stringent conditions" or "stringent hybridization conditions" includes reference to conditions under which a probe will hybridize to its target sequence, to a detectably greater degree than other sequences (e.g., at least 2-fold over background). Stringent conditions are target sequence dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Generally, probes of this type are in a range of about 1000 nucleotides in length to about 250 nucleotides in length.

An extensive guide to the hybridization of nucleic acids is found in Tijssen, *Laboratory Techniques in Biochemistry and Molecular Biology—Hybridization with Nucleic Acid Probes,* Part I, Chapter 2 "Overview of principles of hybridization and the strategy of nucleic acid probe assays", Elsevier, N.Y. (1993); and *Current Protocols in Molecular Biology,* Chapter 2, Ausubel, et al., Eds., Greene Publishing and Wiley-Interscience, New York (1995). See also Sambrook et al. (1989) *Molecular Cloning: A Laboratory Manual* (2nd ed. Cold Spring Harbor Laboratory, Cold Spring Harbor, N.Y.).

In general, sequences that correspond to the promoter sequence of the present invention and hybridize to the promoter sequence disclosed herein will be at least 50% homologous, 70% homologous, and even 85% homologous or more with the disclosed sequence. That is, the sequence similarity between probe and target may range, sharing at least about 50%, about 70%, and even about 85% sequence similarity.

Specificity is typically the function of post-hybridization washes, the critical factors being the ionic strength and temperature of the final wash solution. Generally, stringent wash temperature conditions are selected to be about 5° C. to about 2° C. lower than the melting point ($T_m$) for the specific sequence at a defined ionic strength and pH. The melting point, or denaturation, of DNA occurs over a narrow temperature range and represents the disruption of the double helix into its complementary single strands. The process is described by the temperature of the midpoint of transition, $T_m$, which is also called the melting temperature. Formulas are available in the art for the determination of melting temperatures.

Preferred hybridization conditions for the promoter sequence of the invention include hybridization at 42° C. in 50%(w/v) formamide, 6× SSC, 0.5%(w/v) SDS, 100 µg/ml salmon sperm DNA. Exemplary low stringency washing conditions include hybridization at 42° C. in a solution of 2× SSC, 0.5% (w/v) SDS for 30 minutes and repeating. Exemplary moderate stringency conditions include a wash in 2× SSC, 0.5% (w/v) SDS at 50° C. for 30 minutes and repeating. Exemplary high stringency conditions include a wash in 2× SSC, 0.5% (w/v) SDS, at 65° C. for 30 minutes and repeating. Sequences that correspond to the promoter of the present invention may be obtained using all the above conditions. For purposes of defining the invention, the high stringency conditions are used.

Methods of aligning sequences for comparison are well-known in the art. Gene comparisons can be determined by conducting BLAST (Basic Local Alignment Search Tool; Altschul, S. F., et al., (1993) *J. Mol. Biol.* 215:403–410; see also www.ncbi.nlm.nih.gov/BLAST/) searches under default parameters for identity to sequences contained in the BLAST "GENEMBL" database. A sequence can be analyzed for identity to all publicly available DNA sequences contained in the GENEMBL database using the BLASTN algorithm under the default parameters. Identity to the sequence of the present invention would mean a polynucleotide sequence having at least 65% sequence identity, more preferably at least 70% sequence identity, more preferably at least 75% sequence identity, more preferably at least 80% identity, more preferably at least 85% sequence identity, more preferably at least 90% sequence identity and most preferably at least 95% sequence identity wherein the percent sequence identity is based on the entire promoter region.

Sequence fragments with high percent identity to the sequence of the present invention also refer to those fragments of a particular promoter nucleotide sequence disclosed herein that operate to promote the seed-preferred expression of an operably linked heterologous nucleotide sequence. These fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments can be obtained by use of restriction enzymes to cleave the naturally occurring promoter nucleotide sequences disclosed herein; by synthesizing a nucleotide sequence from the naturally occurring promoter DNA sequence; or can be obtained through the use of PCR technology. See particularly, Mullis et al. (1987) *Methods Enzymol.* 155:335–350, and Erlich, ed. (1989) *PCR Technology* (Stockton Press, N.Y.). Again, variants of these promoter fragments, such as those resulting from site-directed mutagenesis, are encompassed by the compositions of the present invention.

Nucleotide sequences comprising at least about 20 contiguous sequences of the sequence set forth in SEQ ID NO 1 are encompassed. These sequences can be isolated by hybridization, PCR, and the like. Such sequences encompass fragments capable of driving seed-preferred expression, fragments useful as probes to identify similar sequences, as well as elements responsible for temporal or tissue specificity.

Biologically active variants of the promoter sequence are also encompassed by the composition of the present invention. A regulatory "variant" is a modified form of a regulatory sequence wherein one or more bases have been modified, removed or added. For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

One example of a regulatory sequence variant is a promoter formed by one or more deletions from a larger promoter. The 5' portion of a promoter up to the TATA box near the transcription start site can be deleted without abolishing promoter activity, as described by Zhu et al., *The Plant Cell* 7: 1681–89 (1995). Such variants should retain promoter activity, particularly the ability to drive expression in seed or seed tissues. Biologically active variants include, for example, the native promoter sequences of the invention having one or more nucleotide substitutions, deletions or insertions. Promoter activity can be measured by Northern blot analysis, reporter activity measurements when using transcriptional fusions, and the like. See, for example, Sambrook et al. (1989) *Molecular Cloning: A Laboratory Manual* (2nd ed. Cold Spring Harbor Laboratory, Cold Spring Harbor, N.Y.), herein incorporated by reference.

The nucleotide sequence for the promoter of the invention, as well as fragments and variants thereof, can be provided in expression cassettes along with heterologous nucleotide sequences for expression in the plant of interest, more particularly in the seed of the plant. Such an expression cassette is provided with a plurality of restriction sites for insertion of the nucleotide sequence to be under the transcriptional regulation of the promoter.

These expression cassettes are useful in the genetic manipulation of any plant, when operably linked with a heterologous nucleotide sequence whose expression is to be controlled, to achieve a desired phenotypic response. By "operably linked" is intended that the transcription or translation of the heterologous nucleotide sequence is under the influence of the promoter sequence.

The genes of interest expressed by the promoter of the invention can be used for varying the phenotype of seeds. This can be achieved by increasing expression of endogenous or exogenous products in seeds. Alternatively, the results can be achieved by providing for a reduction of expression of one or more endogenous products, particularly enzymes or cofactors in the seed. These modifications result in a change in phenotype of the transformed seed.

General categories of genes of interest for the purposes of the present invention include for example, those genes involved in information, such as Zinc fingers, those involved in communication, such as kinases, and those involved in housekeeping, such as heat shock proteins. More specific categories of transgenes include genes encoding important traits for agronomics, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms. It is recognized that any gene of interest, including the native coding sequence, can be operably linked to the promoter of the invention and expressed in the seed.

Modifications that affect grain traits include increasing the content of oleic acid, or altering levels of saturated and unsaturated fatty acids. Likewise, increasing the levels of lysine and sulfur containing amino acids may be desired as well as the modification of starch type and content in the seed. Hordothionin protein modifications are described in PCT/US94/382 filed Apr. 10, 1997; PCT/US96/08219 filed Mar. 26, 1997; PCT/US96/08220 filed Mar. 26, 1997 and U.S. Pat. No. 5,703,409 issued Dec. 30, 1997; the disclosures of which are incorporated herein by reference. Another example is lysine and/or sulfur rich seed protein encoded by the soybean 2S albumin described in PCT/US97/04409 filed Mar. 20, 1996, and the chymotrypsin inhibitor from barley, Williamson et al. (1987) *Eur. J. Biochem.* 165:99–106, the disclosures of each are incorporated by reference.

Derivatives of the following genes can be made by site directed mutagenesis to increase the level of preselected amino acids in the encoded polypeptide. For example, the gene encoding the barley high lysine polypeptide (BHL), is derived from barley chymotrypsin inhibitor, PCT/US97/20441 filed Nov. 1, 1996 and PCT/US97/20441 filed Oct. 31, 1997, the disclosures of each are incorporated herein by reference. Other proteins include methionine-rich plant proteins such as from sunflower seed, Lilley et al. (1989) *Proceedings of the World Congress on Vegetable Protein Utilization in Human Foods and Animal Feedstuffs;* Applewhite, H. (ed.); American Oil Chemists Soc., Champaign, Ill.:497–502, incorporated herein by reference; corn, Pedersen et al. (1986) *J. Biol. Chem.* 261:6279; Kirihara et al. (1988) *Gene* 71:359, both incorporated herein by reference; and rice, Musumura et al. (1989) *Plant Mol. Biol.* 12:123, incorporated herein by reference. Other important genes encode latex, Floury 2, growth factors, seed storage factors and transcription factors.

Agronomic traits in seeds can be improved by altering expression of genes that affect the response of seed growth and development during environmental stress, Cheikh-N et al (1994) *Plant Physiol.* 106(1):45–51) and genes controlling carbohydrate metabolism to reduce kernel abortion in maize, Zinselmeier et al (1995) *Plant Physiol.* 107(2):385–391.

Insect resistance genes may encode resistance to pests that have great yield drag such as rootworm, cutworm, European Corn Borer, and the like. Such genes include, for example, *Bacillus thuringiensis* endotoxin genes, U.S. Pat. Nos. 5,366,892; 5,747,450; 5,737,514; 5,723,756; 5,593,881; Geiser et al. (1986) *Gene* 48:109; lectins, Van Damme et al. (1994) *Plant Mol. Biol.* 24:825; and the like.

Genes encoding disease resistance traits include detoxification genes, such as against fumonosin (PCT/US95/10284 filed Jun. 7, 1995); avirulence (avr) and disease resistance (R) genes Jones et al. (1994) *Science* 266:789; Martin et al. (1993) *Science* 262:1432; Mindrinos et al. (1994) *Cell* 78:1089; and the like.

Commercial traits can also be encoded on a gene(s) which could alter or increase for example, starch for the production of paper, textiles and ethanol, or provide expression of proteins with other commercial uses. Another important commercial use of transformed plants is the production of polymers and bioplastics such as described in U.S. Pat. No. 5,602,321 issued Feb. 11, 1997. Genes such as B-Ketothiolase, PHBase (polyhydroxyburyrate synthase) and acetoacetyl-CoA reductase (see Schubert et al. (1988) *J. Bacteriol* 170(12):5837–5847) facilitate expression of polyhyroxyalkanoates (PHAs).

The nucleotide sequence operably linked to the promoter disclosed herein can be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the promoter sequence disclosed herein can be operably linked to anti-sense DNA sequences to reduce or inhibit expression of a native protein in the plant seed.

The expression cassette will also include at the 3' terminus of the heterologous nucleotide sequence of interest, a transcriptional and translational termination region functional in plants. The termination region can be native with the promoter nucleotide sequence of the present invention, can be native with the DNA sequence of interest, or can be derived from another source. Convenient termination regions are available from the Ti-plasmid of *A. tumefaciens,* such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acid Res.* 15:9627–9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein et al. (1989) *Proc. Nat. Acad. Sci. USA* 86:6126–6130; potyvirus leaders, for example, TEV leader (Tobacco Etch Virus), Allison et al. (1986); MDMV leader (Maize Dwarf Mosaic Virus), *Virology* 154:9–20; human immunoglobulin heavy-chain binding protein (BiP), Macejak et al. (1991) *Nature* 353:90–94; untranslated leader from the coat protein mRNA of alfalfa mosaic virus (AMV RNA 4), Jobling et al. (1987) *Nature* 325:622–625); tobacco mosaic virus leader (TMV), Gallie et al. (1989) *Molecular Biology of RNA,* pages 237–256; and maize chlorotic mottle virus leader (MCMV) Lommel et al. (1991) *Virology* 81:382–385. See also Della-Cioppa et al. (1987) *Plant Physiology* 84:965–968. The cassette can also contain sequences that enhance translation and/or mRNA stability such as introns.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

As noted herein, the present invention provides vectors capable of expressing genes of interest under the control of the promoter. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The transformation vector comprising the promoter sequence of the present invention operably linked to a heterologous nucleotide sequence in an expression cassette, can also contain at least one additional nucleotide sequence for a gene to be cotransformed into the organism. Alternatively, the additional sequence(s) can be provided on another transformation vector.

Vectors that are functional in plants can be binary plasmids derived from Agrobacterium. Such vectors are capable of transforming plant cells. These vectors contain left and right border sequences that are required for integration into the host (plant) chromosome. At minimum, between these border sequences is the gene to be expressed under control of the promoter. In preferred embodiments, a selectable marker and a reporter gene are also included. For ease of obtaining sufficient quantities of vector, a bacterial origin that allows replication in *E. coli* is preferred.

Reporter genes can be included in the transformation vectors. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. (1987) *Mol. Cell. Biol.* 7:725–737; Goff et al. (1990) *EMBO J.* 9:2517–2522; Kain et al. (1995) *Bio Techniques* 19:650–655; and Chiu et al. (1996) *Current Biology* 6:325–330.

Selectable marker genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. (1983) *EMBO J.* 2:987–992; methotrexate, Herrera Estrella et al. (1983) *Nature* 303:209–213; Meijer et al. (1991) *Plant Mol. Biol.* 16:807–820; hygromycin, Waldron et al. (1985) *Plant Mol. Biol.* 5:103–108; Zhijian et al. (1995) *Plant Science* 108:219–227; streptomycin, Jones et al. (1987) *Mol. Gen. Genet.* 210:86–91; spectinomycin, Bretagne-Sagnard et al. (1996) *Transgenic Res.* 5:131–137; bleomycin, Hille et al. (1990) *Plant Mol. Biol.* 7:171–176; sulfonamide, Guerineau et al. (1990) *Plant Mol. Biol.* 15:127–136; bromoxynil, Stalker et al. (1988) *Science* 242:419–423; glyphosate, Shaw et al. (1986) *Science* 233:478–481; phosphinothricin, DeBlock et al. (1987) *EMBO J.* 6:2513–2518.

Other genes that could serve utility in the recovery of transgenic events but might not be required in the final product would include, but are not limited to, examples such as GUS (β-glucoronidase), Jefferson (1987) *Plant Mol Biol. Rep.* 5:387); GFP (green florescence protein), Chalfie et al. (1994) *Science* 263:802; luciferase, Teeri et al. (1989) *EMBO J.* 8:343; and the maize genes encoding for anthocyanin production, Ludwig et al. (1990) *Science* 247:449.

The transformation vector comprising the particular promoter sequence of the present invention, operably linked to a heterologous nucleotide sequence of interest in an expression cassette, can be used to transform any plant. In this manner, genetically modified plants, plant cells, plant tissue, seed, and the like can be obtained. Transformation protocols can vary depending on the type of plant or plant cell, i.e., monocot or dicot, targeted for transformation. Suitable methods of transforming plant cells include microinjection, Crossway et al. (1986) *Biotechniques* 4:320–334; electroporation, Riggs et al. (1986) *Proc. Natl. Acad. Sci. USA* 83:5602–5606; Agrobacterium-mediated transformation, see for example, Townsend et al. U.S. Pat. No. 5,563,055; direct gene transfer, Paszkowski et al. (1984) *EMBO J.* 3:2717–2722; and ballistic particle acceleration, see for example, Sanford et al. U.S. Pat. No. 4,945,050; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923–926. Also see Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Datta etal. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Klein et al. (1988) *Plant Physiol.* 91:440–444 (maize); Fromm et al. (1990) *Biotechnology* 8:833–839; Hooydaas-Van Slogteren et al (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. G. P. Chapman et al. (Longman, N.Y.), pp. 197–209 (pollen); Kaeppler et al. (1990) *Plant Cell Reports* 9:415–418; and Kaeppler et al. (1992) *Theor. Appl. Genet.* 84:560–566 (whisker-mediated transformation); D. Halluin et al. (1992) *Plant Cell* 4:1495–1505 (electroporation); Li et al. (1993) *Plant Cell Reports* 12:250–255 and Christou et al. (1995) *Annals of Botany* 75:407–413 (rice); Osjoda et al. (1996) *Nature Biotechnology* 14:745–750 (maize via Agrobacterium tumefaciens); all of which are herein incorporated by reference.

The cells that have been transformed can be grown into plants in accordance with conventional ways. See, for example, McCormick et al. (1986) *Plant Cell Reports* 5:81–84. These plants can then be grown, and pollinated with the same transformed strain or different strains. The resulting hybrid having seed-preferred expression of the desired phenotypic characteristic can then be identified. Two or more generations can be grown to ensure that seed-preferred expression of the desired phenotypic characteristic is stably maintained and inherited.

The following examples are offered by way of illustration and not by way of limitation.

EXPERIMENTAL

The promoter region for the soybean gene AL3 was isolated from soybean plants and cloned. This gene was selected as a source for a seed-preferred promoter based on the spatial expression of its gene products. The method for its isolation is described below.

EXAMPLE 1

Isolation of Regulatory Sequences From a Soybean AL3 Gene Using Promoter Adapter Mediated Capture Soybean genomic DNA was completely digested with TaqI. Any RNA present was removed by RNase treatment. Sequences were chosen to anneal with the CG extension provided by the TaqI digest of the genomic DNA. (The TaqI site is lost when an adapter becomes ligated to genomic DNA.)

SEQ ID No:2 5' CTACTACTACTAGACGGCTGCACGCT-GATACGAC3'

SEQ ID No:3 5' CGGTCGTATCAGCGT3'

Equimolar amounts of oligonucleotides SEQ ID NOS 2 and 3 were incubated under annealing conditions to form the adapter. The adapter was ligated to the purified TaqI digested soybean genomic DNA in the presence of TaqI. The reaction was heated to 65° C. for 20 minutes to inactivate the ligase and to melt the association with oligonucleotide SEQ ID No:3. The reaction products were purified by GlassMAX® DNA Isolation Spin Cartridge. The purified adapter-ligated DNA "library" then served as a template for subsequent PCR reactions. Primary PCR reactions were performed using the Advantage™ cDNA PCR Kit (Clontech). The manufacturer's reaction conditions were followed, using 1μl (60 ng) of the adapter "library" and a final concentration of 0.3 μM of the gene-specific oligonucleotide:
SEQ ID No:4 5' CTTGGATCTTCTCCATGATGTGC3'

Cycle conditions were: 94° C. for 2 minutes; 94° C. for 30 seconds; 60° C. for 40 seconds over 30 cycles; 68° C. for 90 seconds and 68° C. for 3 minutes. Secondary PCR was performed as above using 1 μl of the primary PCR reaction as template with the oligonucleotide pair comprised of oligonucleotide SEQ ID NOS. 2 and 4.
SEQ ID No: 5 5' GAGAAGAGAGATGAGGAGGATTGT-GAACTTGGTCAT 3'

Secondary PCR was performed as above using oligonucleotide SEQ ID No:5 with oligonucleotide SEQ ID No.:2. The reaction products were separated on a 1% agarose gel and then purified by a GlassMAX™ DNA Isolation Spin Cartridge. The purified fragments were cloned into TA cloning vector pCR2.1 (Invitrogen, Carlsbad, Calif.) and completely sequenced on an ABI 377 sequencer (Perkin-Elmer, Foster City, Calif.).

EXAMPLE 2

Expression Data Using Promoter Sequence

A DNA sequence 5' from the coding regions of the soybean AL3 gene was placed upstream of the *E. coli* β-glucuronidase gene (from the uldA locus) in the plasmid pBI121 as described by Jefferson Id. Plasmid pBI121 is a BIN19 derivative that contains the CaMV 35S promoter 5' to the β-glucuronidase coding region, and a plant selectable marker (kan$^r$), both being between the tDNA borders required for transfer of DNA into plant cells via *Agrobacterium tumefaciens*. The CaMV 35S promoter was removed by a HindIII/BamHI digest. The 5' flanking region of the AL3 gene was ligated into the Hind III/Bam HI sites of the 'promoterless' pBI121 to create AL3 promoter::pBI121.

Two promoter constructs were prepared: (i) the AL3 promoter; and (ii) a construct created by the insertion of the *Ricinus communis* DnaJ intron as described by U.S. patent application Ser. No. 06/098,690 previously incorporated by reference; between the 5' flanking region and the GUS gene as a BamHI/SmaI fragment. These constructs were used to transform tobacco leaf disks via *Agrobacterium tumefaciens*-mediated transformation as described by U.S. Pat. No. 5,591,616. Histochemical analysis of tissue sections of kan$^r$ plants are performed by adding 100 mg of the substrate, 5-bromo-4-chloro-3-indoyl glycuronide sodium salt (Biosynth A. G., Staad, Switzerland) in 2 ml of DMSO (Sigma, St. Louis, Mo.) to 200 mL of 10 mM EDTA (Na+2)2, 0.1% Triton X-100, 0.1 M sodium phosphate pH 7.0, and 0.5 mM potassium ferrocyanide. Plant tissue is incubated in the above mixture at 37° C. overnight and β-glucuronidase activity is determined colorimetrically (Jefferson, Id.).

EXAMPLE 3

Northern Analysis of Gene Expression in Developing Seeds

Total RNA (10 μg) was size fractionated on a 1% formaldehyde agarose gel and transferred to a nylon membrane. Membranes were hybridized under stringent conditions with a $^{32}$P-labelled probe representing a cDNA fragment of the gene. After extensive washing to remove unbound probe, the membrane was exposed on X-ray film. The developed film showed the AL3 gene predominately expressed in seed from 24 to 40 days after flowering.

EXAMPLE 4

In situ localization of AL3 mRNA in Developing Soybean Seed

In situ hybridization was performed using both a sense and antisense mRNA probe corresponding to an mRNA of the AL3 cDNA. Probes were labeled non-isotopically with digoxigenin and incubated with various sections of 13 to 70 DAF soybean seed which had been fixed and embedded. Following extensive washing to remove unbound probe, sections were incubated with anti-digoxigenein alkaline phosphatase to detect areas of probe hybridization. For AL3, mRNA was detected specifically with the antisense probe in 24 to 40 DAF seeds; was restricted to cotyledon, cortex and endosperm remnant tissues and excluded from the seed coat and conductive tissues. The sense control probe did not hybridize.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications can be practiced within the scope of the appended claims.

That which is claimed:

1. An isolated promoter that comprises nucleotide sequences having at least 65% sequence identity to SEQ ID NO: 1 wherein the % sequence identity is based on the entire sequence and is determined by BLAST analysis under default parameters and said isolated promoter has the transcription initiating properties of SEQ ID NO: 1.

2. An isolated promoter that comprises a nucleotide sequence as set forth in SEQ ID NO: 1.

3. An expression cassette comprising a promoter and a nucleotide sequence of interest operably linked to the promoter, wherein the promoter comprises the nucleotide sequence set forth in SEQ ID NO: 1.

4. An expression cassette comprising a promoter and a nucleotide sequence of interest operably linked to the promoter, wherein the promoter has at least 65% sequence identity to SEQ ID NO: 1, wherein the % sequence identity is based on the entire sequence and is determined by BLAST analysis under default parameters and said promoter has the transcription initiating properties of SEQ ID NO: 1.

5. A transformation vector comprising the expression cassette of claim 4.

6. A plant cell tranformed with the expression cassette of claim 4.

7. A plant stably transformed with the expression cassette of claim 4.

8. A method for selectively expressing a nucleotide sequence of interest in a plant seed, the method comprising:

(a) introducing the expression cassette of claim 4 into a plant cell;

(b) producing a plant from said plant cells; and (c) inducing expression of said nucleotide for a time sufficient to express the nucleotide sequence in the plant seed.

9. The plant of claim 7, wherein said plant is a dicot.

10. The plant of claim 9 wherein the dicot is soybean, alfalfa, safflower, tobacco, sunflower, cotton, or canola.

11. Seeds of the plants of claim 7.

12. The method of claim 8, wherein said nucleotide sequence encodes a polynucleotide involved in fatty acid synthesis.

13. The method of claim 8, wherein said nucleotide sequence encodes a polypeptide having enhanced amino acid content.

14. The plant cell of claim 6, wherein said plant cell is from a dicot.

15. The plant cell of claim 6, wherein said plant cell is from soybean, alfalfa, tobacco, safflower, sunflower, cotton, or canola.

* * * * *

SEQUENCE LISTING

<160> NUMBER OF SEQ ID NOS: 5

<210> SEQ ID NO 1
<211> LENGTH: 1145
<212> TYPE: DNA

-continued

```
<213> ORGANISM: Glycine max

<400> SEQUENCE: 1
ctactactac tacggctgca cgctgatacg accgatagaa ctgctacgga tagctcctcc      60
attgcgctct ctctgttttc cttctttctt ctctctggtt tctcgcgaaa ttggtttccc     120
aactgcgttt ggggctccag attaaacgac gccgtttcgt tcctttcgct tcacggctta    180
acgatgtcgt ttctgtctgt gcccaaaaaa taaaggcatt tgttatttgc accagatatt    240
tactaagtgc accctagttt gacaagtagg cgataattac aaatagatgc ggtgcaaata    300
ataaattttg aaggaaataa ttacaaaaga acagaactta tatttacttt attttaaaaa    360
actaaaatga agaacaaaa aagtaaaaa atacaaaaaa tgtgctttaa ccactttcat      420
tatttgttac agaaagtatg attctactca aattgatctg ttgtatctgg tgctgccttg    480
tcacactggc gatttcaatc ccctaaagat atggtgcaaa ctgcgaagtg atcaatatct    540
gctcggttaa tttagattaa ttaataatat tcaacgtgat gtaccaaaaa aagacaattt    600
tttgctccat tgacaaatta aacctcatca aggtaatttc caaacctata agcaaaaaaa    660
tttcacatta attggcccgc aatcctatta gtcttattat actagagtag gaaaaaaaac    720
aattacacaa cttgtcttat tattctctat gctaatgaat attttttccct tttgttagaa    780 atcagtgttt cctaatttat tgagtattaa ttccactcac cgcatatatt taccgttgaa    840
taagaaaatt ttcacataa ttctttttaa gataaataat tttttttatac tagatcttat    900 atgattacgt gaagccaagt gggttatact aatgatatat aatgtttgat agtaatcagt    960
ttataaacca aatgcatgga aatgttacgt ggaagcacgt aaattaacaa gcattgaagc   1020
aaatgcagcc accgcaccaa aaccacccca cttcacttcc acgtaccata ttccatgcaa   1080
ctacaacacc ctaaaacttc aataaatgcc cccaccttca cttcacttca cccatcaata   1140
gcaag                                                                1145

<210> SEQ ID NO 2
<211> LENGTH: 34
<212> TYPE: DNA
<213> ORGANISM: Artificial Sequence
<220> FEATURE:
<221> NAME/KEY: primer_bind
<222> LOCATION: (1)...(34)

<400> SEQUENCE: 2
ctactactac tagacggctg cacgctgata cgac                                  34

<210> SEQ ID NO 3
<211> LENGTH: 15
<212> TYPE: DNA
<213> ORGANISM: Artificial Sequence
<220> FEATURE:
<221> NAME/KEY: primer_bind
<222> LOCATION: (1)...(15)

<400> SEQUENCE: 3
cggtcgtatc agcgt                                                       15

<210> SEQ ID NO 4
<211> LENGTH: 23
<212> TYPE: DNA
<213> ORGANISM: Artificial Sequence
<220> FEATURE:
<221> NAME/KEY: primer_bind
<222> LOCATION: (1)...(23)
```

```
-continued

<400> SEQUENCE: 4
cttggatctt ctccatgatg tgc                                              23

<210> SEQ ID NO 5
<211> LENGTH: 36
<212> TYPE: DNA
<213> ORGANISM: Artificial Sequence
<220> FEATURE:
<221> NAME/KEY: primer_bind
<222> LOCATION: (1)...(36)

<400> SEQUENCE: 5 gaagagag atgaggagga ttgtgaactt ggtcat                                  36
```